United States Patent [19]

Yamasaki et al.

[11] Patent Number: 5,090,258
[45] Date of Patent: Feb. 25, 1992

[54] MULTIPLE FLOW-DIVIDING DILUTION TUNNEL SYSTEM

[75] Inventors: Akira Yamasaki, Tokyo; Yoshinaka Takeda, Yokohama; Souhei Abe, Funabashi; Izumi Fukano, Yokohama, all of Japan

[73] Assignee: Mitsubishi Jidosha Kogyo Kabushiki Kaisha, Tokyo, Japan

[21] Appl. No.: 590,132

[22] Filed: Sep. 28, 1990

[30] Foreign Application Priority Data

Sep. 29, 1989 [JP] Japan .................. 1-114649[U]
May 22, 1990 [JP] Japan .................. 2-53353
Sep. 20, 1990 [JP] Japan .................. 2-251262[U]

[51] Int. Cl.$^5$ .................................................. G01N 1/00
[52] U.S. Cl. .................................................. 73/863.03
[58] Field of Search .......................... 73/23.31–23.33, 73/863.02, 863.03, 864.81, 863.41, 863.43, 863.58

[56] References Cited

U.S. PATENT DOCUMENTS 3,478,600 11/1969 Lynn .................. 73/863.03
4,586,367 5/1986 Lewis .................. 73/23.33
4,633,706 1/1987 Ito et al. .................. 73/23.33

Primary Examiner—Robert Raevis
Attorney, Agent, or Firm—Oblon, Spivak, McClelland, Maier & Neustadt

[57] ABSTRACT

A multipipe flow-dividing dilution tunnel system divides a gas to be inspected, such as an automobile exhaust gas, at a predetermined division ratio, dilutes a divided gas with a dilution gas, and samples and tests the diluted gas for particulate materials and other constituents. The gas to be inspected is introduced into a multipipe flow divider having a plurality of flow-dividing pipes, one of which extends as an inlet pipe into a dilution tunnel. The gas is divided by the inlet pipe and introduced therethrough into the dilution tunnel. A plurality of division ratio control nozzles are disposed in the dilution tunnel immediately downstream of the outlet of the inlet pipe for ejecting for ejecting a pressurized dilution gas toward a position downstream of the outlet of the inlet pipe. The ejected dilution gas gives, to the inlet pipe, a pressure loss equal to fluctuations of the pressure loss caused by the multipipe flow divider, so that a static pressure at the outlet of the inlet pipe and a static pressure at the outlet of the flow divider will be equalized. The ratio of the rate of the divided gas introduced through the inlet pipe into the dilution tunnel to the rate of the total gas introduced into the system is thus rendered constant at all times. Irrespective of fluctuations of the rate of the total gas introduced into the system, the gas can always be divided at a constant division ratio for accurate examination of its components or constituents.

6 Claims, 11 Drawing Sheets

MULTIPLE FLOW-DIVIDING DILUTION TUNNEL SYSTEM

BACKGROUND OF THE INVENTION

The present invention relates to a multipipe flow-dividing dilution tunnel system for dividing a gas to be inspected at a predetermined division ratio, diluting a divided gas, and sampling and testing the diluted gas for its components or constituents.

For the purpose of reducing air pollution caused by automobile emissions, it is necessary to sample automobile exhaust gases and analyze particulate materials contained in the exhaust gases and other components thereof. Total dilution tunnel systems which are used to dilute the total amount of sampled exhaust gases are large in scale and requires a large expenditure of expenses. In view of this, there has been proposed a flow-dividing dilution tunnel system which employs a small-size dilution tunnel for diluting a divided flow of exhaust gases.

FIG. 14 of the accompanying drawings illustrates a conventional flow-dividing dilution tunnel system. In the conventional flow-dividing dilution tunnel system, the exhaust gas emitted from an automobile engine is introduced into a surge tank 3 through a multipipe flow divider 2 which comprises a plurality of flow-dividing pipes 1 having the same diameter and length. The exhaust gas is thereafter discharged from the surge tank 3 through a flue 17. One of the flow-dividing tubes 1 extends out of the flow divider 2 and has a downstream end portion introduced as an inlet pipe 4 into a dilution tunnel 5. The dilution tunnel 5 has a constant-rate suction device 6 in its downstream end. The suction device 6 draws ambient air from the upstream end of the dilution tunnel 5 through a rate regulating butterfly valve 24 into the dilution tunnel 5. The divided exhaust gas which has been introduced through the inlet pipe 4 into the dilution tunnel 5 is diluted by air, or a dilution gas, from the butterfly valve 24 in a position immediately upstream of a mixing orifice 7. Fine particles of the diluted gas are passed through a corrective filter 30 and sampled by a constant-rate sampling device 31, or analyzed by an exhaust gas analyzer 32.

The flow-dividing dilution tunnel system shown in FIG. 14 can introduce a divided exhaust gas into the dilution tunnel 5 through the inlet pipe 4 at a division ratio which is equal to the ratio of the number of the inlet pipe 4 to the number of the flow-dividing pipes 1. The introduced exhaust gas is diluted by dilution air, and the diluted gas is thereafter sampled and analyzed for its constituents.

However, when the output power of the automobile engine varies, the pressure loss of the multipipe flow divider 2 also varies, resulting in fluctuations of the ratio of the amount of the divided exhaust gas which is introduced into the dilution tunnel 5 through the inlet pipe 4 to the amount of the total exhaust gas flowing into the flow divider 2. When this happens, the diluted exhaust gas cannot be accurately analyzed for its constituents. This problem may be solved when a pressure loss, equal to a variation in the pressure loss of the multipipe flow divider 2 due to a change in the total amount of the introduced exhaust gas, is given to the inlet pipe 4.

SUMMARY OF THE INVENTION

It is an object of the present invention to provide a highly accurate multipipe flow-dividing dilution tunnel system which can introduce, into a dilution tunnel, an exhaust gas to be inspected that has been divided at an accurate division ratio equal to the ratio of the number of an inlet pipe to the number of flow-dividing pipes, irrespective of fluctuations of the total amount of an exhaust gas from which the exhaust gas to be inspected has been divided, so that the exhaust gas can be tested highly accurately for its components or constituents.

Another object of the present invention is to provide a highly accurate multipipe flow-divinding dilution tunnel system which has a control means for automatically equalizing the static pressure at the outlet of an inlet pipe and the static pressure at the outlet of a multipipe flow divider to each other, thereby to divide an exhaust gas at an accurate division ratio equal to the ratio of the number of the inlet pipe to the number of flow-dividing pipes, and which introduces the divided exhaust gas into a dilution tunnel so as to be tested highly accurately for its components or constituents.

According to the present invention, a multipipe flow-dividing dilution tunnel system has a multipipe flow divider, a plurality of division ratio control nozzles, a plurality of static pressure detectors, a surge tank, a butterfly valve, and a controller.

The multipipe flow divider comprises a plurality of parallel flow-dividing pipes, one of which extends as an inlet pipe into a dilution tunnel. An exhaust gas which is divided by the inlet pipe at a division ratio, corresponding to the ratio of the number of the inlet pipe to the number of the flow-dividing pipes, is introduced through the inlet pipe into the dilution tunnel.

The division ratio control nozzles are disposed in the dilution tunnel immediately downstream of an outlet of the inlet pipe and arranged symmetrically around a central axis of the outlet of the inlet pipe, the division ratio control nozzles having respective nozzle holes for ejecting a pressurized dilution gas toward a position downstream of the outlet of the inlet pipe. The division ratio control valves has a central axis which is angularly spaced from the central axis of the outlet of the inlet pipe by an angle ranging from 40° to 50°. As the pressure of the dilution gas ejected from the division ratio control nozzles increases, the static pressure at the outlet of the inlet pipe linearly varies, and hence can well be controlled.

The static pressure detectors are disposed respectively at the outlet of the inlet pipe and the outlet of the multipipe flow divider, for detecting information as to the static pressures at the outlet of the inlet pipe and the outlet of the flow divider.

The static pressure detectors are positioned upstream from outlet ends of the inlet pipe and the multipipe flow divider by a distance which is equal to at least the inside diameter of the flow-dividing pipes including the inlet pipe, or each of the static pressure detectors has a plurality of detector units equally spaced axially from outlet ends of the inlet pipe and the multipipe flow divider, for transmitting average static pressure information to the controller, so that variations in the detected static pressures can be eliminated.

The surge tank combines exhaust gases emitted from the flow-dividing pipes of the multipipe flow divider, and supplies the combined exhaust gases to a passage such as a flue vented to atmosphere.

The butterfly can regulate the pressure difference between the surge tank and the passage, and can particularly increase the static pressure at the outlets of the flow-dividing pipes of the multipipe flow divider to a level higher than the static pressure at the outlet of the inlet pipe.

The discharge rate control valve which increases and reduces the rate at which a dilution gas is ejected from the division ratio condition nozzles into the dilution tunnel is connected to the controller. To the discharge rate control valve, there is connected to a source of a pressurized dilution gas for supplying the dilution gas. The controller controls the opening of the discharge rate control valve such that the static pressure at the outlet of the inlet pipe and the static pressure at the outlet of the multipipe flow divider.

The pressurized dilution gas is ejected toward the downstream outlet of the inlet pipe to equalize the static pressure at the outlet of the inlet pipe and the static pressure at the outlet of the multipipe flow divider. Therefore, irrespective of fluctuations of the rate at which the exhaust gas is introduced into the multipipe flow-dividing dilution tunnel system, the exhaust gas can be divided at a constant division ratio at all times. The divided exhaust gas is thereafter diluted in the dilution tunnel, and then the diluted exhaust gas is sampled and analyzed for its components or constituents.

In response to the information as to the static pressure at the outlet of the inlet pipe and the outlet of the multipipe flow divider, the controller controls the discharge rate control valve to increase or reduce the rate at which the dilution gas is ejected through the division ratio control valves into the dilution tunnel, for thereby automatically equalizing the static pressure at the outlet of the inlet pipe and the static pressure at the outlet of the multipipe flow divider. Consequently, the exhaust gas can always be divided at a constant ratio, and the divided exhaust gas is diluted, sampled, and tested for its constituents.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
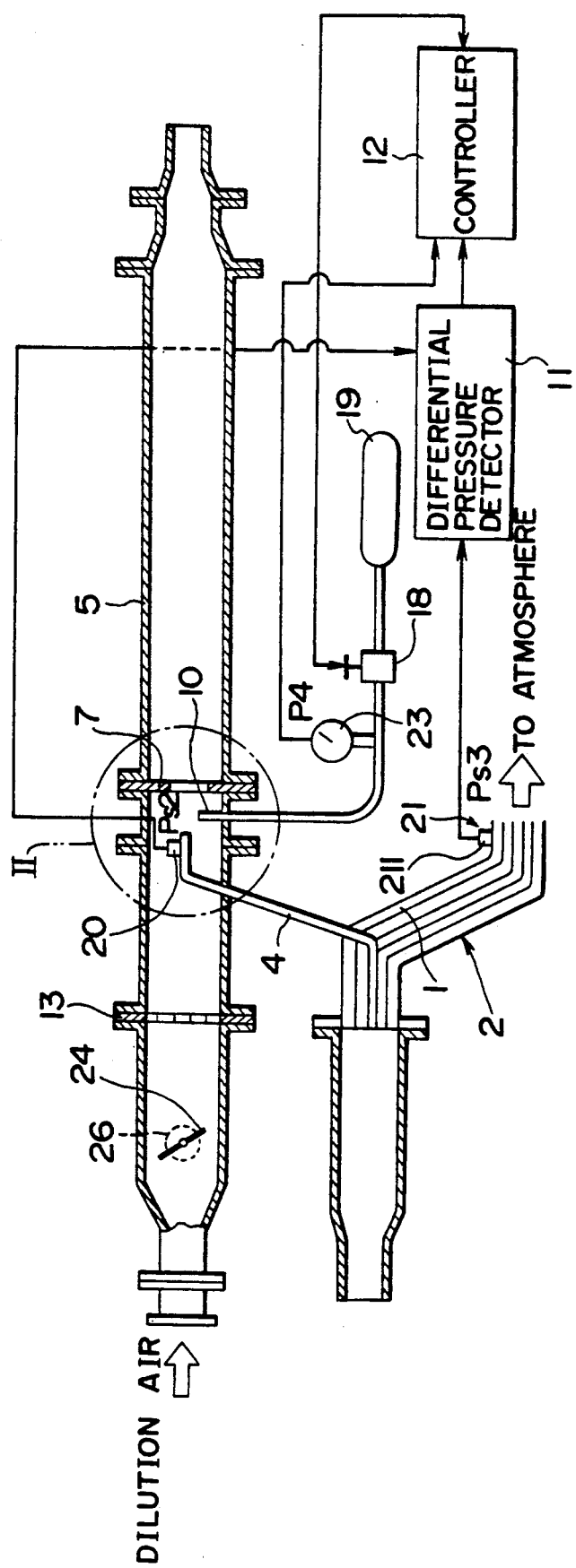
FIG. 1 is a schematic cross-sectional view, partly in block form, of a multipipe flow-dividing dilution tunnel system according to an embodiment of the present invention.

FIG. 1 schematically shows a multipipe flow-dividing dilution tunnel system according to an embodiment of the present invention.

The exhaust gas emitted from an automobile engine is introduced into a multipipe flow divider 2 which comprises a plurality of flow-dividing pipes 1 having the same diameter and length. The exhaust gas is thereafter discharged into atmosphere from the flow divider 2. One of the flow-dividing tubes 1 extends out of the flow divider 2 and has a downstream end portion introduced as an inlet pipe 4 into a dilution tunnel 5. Ambient air is introduced as dilution air into the dilution tunnel 5 from its upstream end through a rate regulating butterfly valve 24 disposed in the dilution tunnel 5. The divided exhaust gas which has been introduced through the inlet pipe 4 into the dilution tunnel 5 is diluted by dilution air from the butterfly valve 24 in a position immediately upstream of a mixing orifice 7.

Between the downstream end of the inlet pipe 4 and the mixing orifice 7, there are disposed a plurality of division ratio control nozzles 10 (only one shown in FIG. 1) positioned in the dilution tunnel 5 and connected through pipes to a pressurized dilution gas source 19 which is located outside of the dilution tunnel 5, through a discharge rate control valve 18 which increases or reduces the rate at which a pressurized dilution gas is discharged from the division ratio control nozzles 10. The division ratio control valves 10 are arranged symmetrically around the central axis of the downstream outlet end of the inlet pipe 4. A flow-rectifying plate 13 is disposed in the dilution tunnel 5 between the butterfly valve 24 and the inlet pipe 4.

The discharge rate control valve 18 may comprise an electropneumatic transducer for increasing and reducing the pressure of a pressurized dilution gas depending on an electric signal Du applied thereto. The pressurized dilution gas may be pressurized air, and the pressurized dilution gas source 19 may comprise an air tank or the like which is supplied with air under pressure from time to time.

The multipipe flow-dividing dilution tunnel system shown in FIG. 1 includes static pressure detectors 20, 21 for detecting a static pressure Ps2 at the outlet of the inlet pipe 4 and a static pressure Ps3 at the outlet of the multipipe flow divider 2, respectively. The multipipe flow-dividing dilution tunnel system also has a static pressure detector 23 for detecting the pressure Ps4 of the pressurized dilution gas. Detected signals from the static pressure detectors 20, 21 are applied to a controller 12 through a differential pressure detector 11. A detected signal from the static pressure detector 23 is directly sent to the controller 12.

Figure 2:
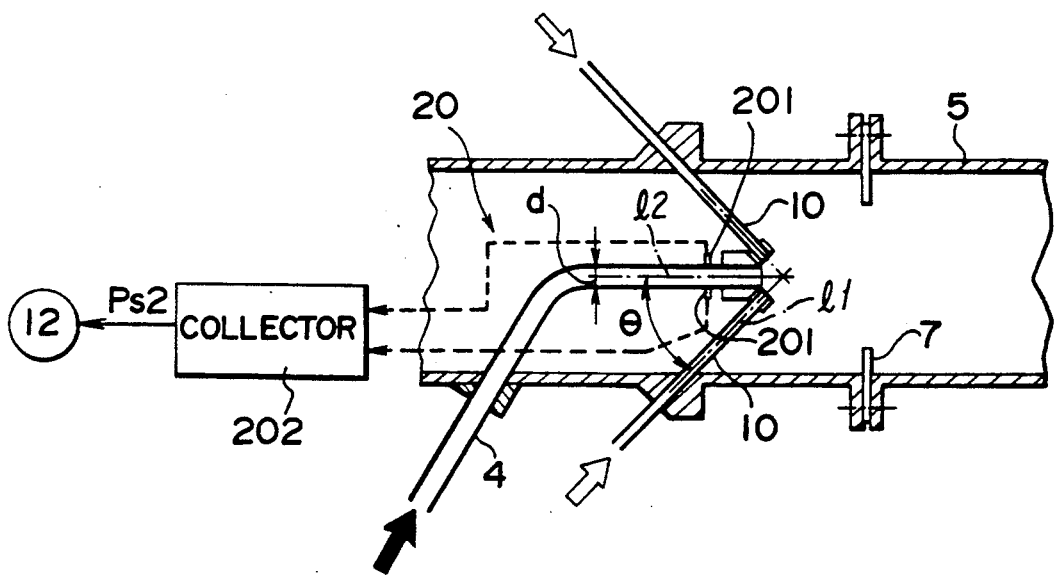
FIG. 2 is a fragmentary cross-sectional view of a static pressure detector in the multipipe flow-dividing dilution tunnel system shown in FIG. 1.

As shown in FIG. 2, the static pressure detector 20 has a plurality of detector units 201 disposed on the inlet pipe 4 at a position which is spaced upstream from the outlet end of the inlet pipe 4 by a distance greater than the inside diameter d of the inlet pipe 4 (the distance is about 2×d in this embodiment). This arrangement of the detector unit 201 is effective in reducing detected pressure fluctuations which would otherwise be caused by pressure pulsations. In this embodiment, four detector units 201 are angularly spaced in the circumferential direction of the inlet pipe 4, but equally spaced axially from the outlet end of the inlet pipe 4. However, only two of the detector units 201 are shown in FIG. 2. The detector units 201 are connected together by a collector 202 which is spaced from the detector units 201 by a certain distance. The static pressures introduced from the detector units 201 are averaged by the collector 202, and the average static pressure is used as the static pressure Ps2. The detectors units 201 and the collector 202 coact with each other to reduce any variations or fluctuations in the detected static pressure, so that highly reliable pressure information can be produced by the static pressure detector 20.

The static pressure detector 21 is of the same construction as shown in FIG. 2, and will not be described in detail.

As shown in FIG. 1, the butterfly valve 24 can be moved between open and closed positions by a conventional electric actuator 26 which is controlled by the controller 12.

As shown in FIGS. 4(A), 4(B) and 5(A), 5(B), the pipes connected to the respective division ratio control nozzles 10 extend through the wall of the dilution tunnel 5. Each of the division ratio control nozzles 10 has a central axis 11 which is angularly spaced by an angle $\theta$ (which is 45° for the reasons described below) from a central axis 12 of the downstream outlet end of the inlet pipe 4. Each of the division ratio control nozzles 10 has a nozzle hole spaced from the downstream outlet end of the inlet pipe 4 by a distance X. The division ratio control nozzles 10 are disposed in confronting relation to each other around the central axis 12 of the outlet of the inlet pipe 4, and symmetrically directed toward a position downstream of the outlet end of the inlet pipe 4.

There are eight division ratio control nozzles 10 each having an inside diameter of about 2 mm, and the inlet pipe 4 has an inside diameter of about 10 mm. The nozzle holes of the division ratio control nozzles 10 are spaced 10 mm from the downstream outlet end of the inlet pipe 4 (see FIG. 4B).

Figure 7:
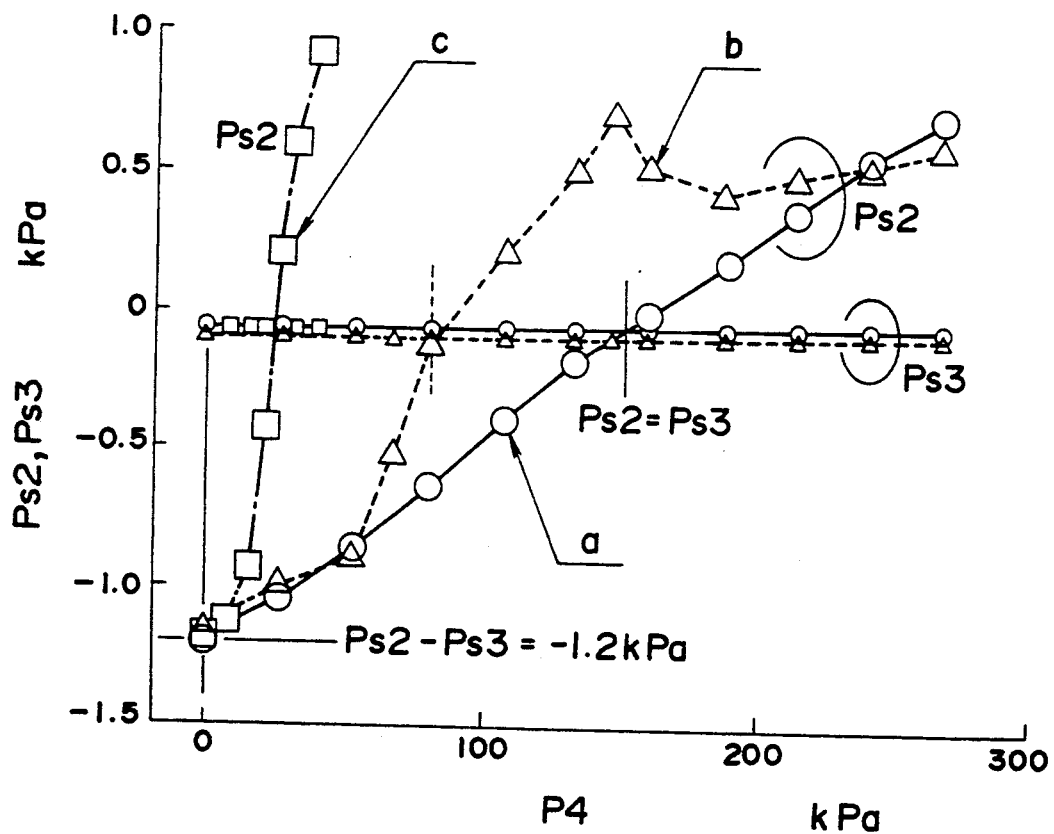
FIG. 7 is a diagram showing static pressures at the outlet of an inlet pipe in the arrangements shown in FIGS. 6A, 6B, and 6C, respectively.

With the parameters of the division ratio control nozzles 10 being thus established, when the pressurized dilution gas pressure P4 is regulated by the discharge rate control valve 18, the static pressure Ps2 at the outlet of the inlet pipe 4 and the static pressure Ps3 at the outlet of the multipipe flow divider 2 vary according to a curve a in FIG. 7. Since the static pressure Ps2 at the outlet of the inlet pipe 4 varies substantially linearly with respect to the pressurized dilution gas pressure P4, the static pressure Ps2 can be well controlled such that it is equalized to the static pressure Ps3 at the outlet of the multipipe flow divider 2.

The angle $\theta$ between the central axes 11 of the division ratio control nozzles 10 and the central axis 12 of the outlet of the inlet pipe 4 may be in the range of $0° \leq \theta \leq 180°$.

Figure 6A:
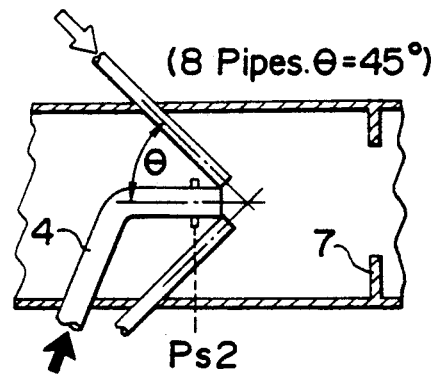
FIGS. 6A, 6B, and 6C are fragmentary cross-sectional views showing different division ratio control nozzles, respectively.
Figure 6B:
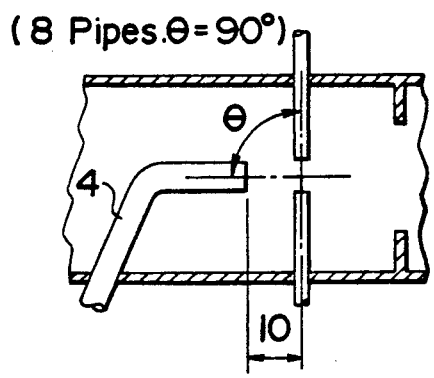
Figure 6C:
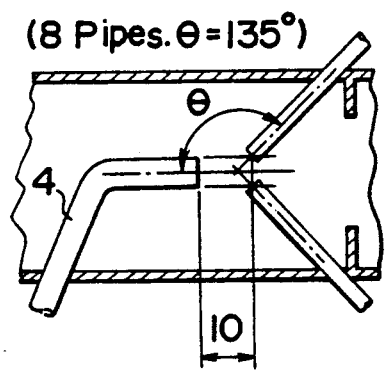

FIG. 6A shows division ratio control valves with the angle $\theta$ being about 45°±5°. FIG. 6B shows division ratio control valves with the angle $\theta$ being in the vicinity of 90°. FIG. 6C shows division ratio control valves with the angle $\theta$ being about 135°. The static pressure Ps2 varies with respect to the pressurized dilution gas pressure P4 according to widely different patterns with these different division ratio control valve arrangements shown in FIGS. 6A, 6B, and 6C.

More specifically, the static pressure Ps2 varies linearly and can easily be controlled with the arrangement shown in FIG. 6A. With the arrangement shown in FIG. 6B, however, the static pressure Ps2 varies nonlinearly and cannot well be controlled at and near its peak vlaue.

According to the arrangement shown in FIG. 6C, the static pressure Ps2 varies nonlinearly by a large extent, and cannot well be controlled. When the flows ejected from the inlet pipe 4 and the division ratio control nozzles 10 impinge upon each other, if the angle $\theta$ were too small, the static pressure Ps2 could not easily be increased, and if the angle $\theta$ were too large, the combined flow produced after the respective flows impinge upon each other would spread through a large angle, tending to produce flow pulsations which could not well be controlled. If the combined flow spread through a large angle, then a portion of the combined flow would impinge upon the orifice 7, a condition which would not be suitable for the measurement of particulate materials.

Figure 8:
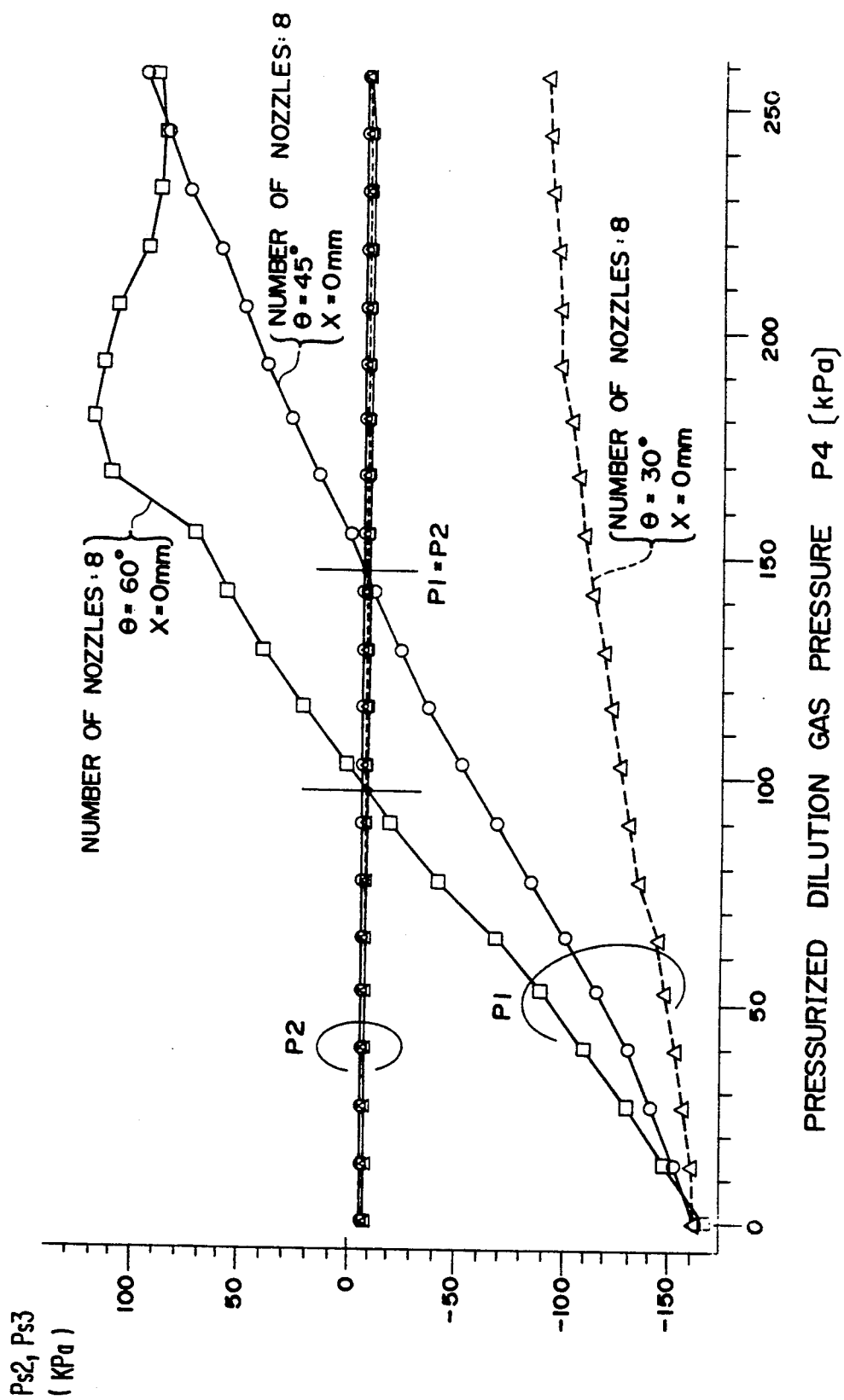
FIGS. 8 and 9 are diagrams each showing the relationship between a dilution gas pressure, a static pressure at the outlet of an inlet pipe, and a static pressure at the outlet of a multipipe flow divider in the multipipe flow-dividing dilution tunnel system shown in FIG. 1.
Figure 9:
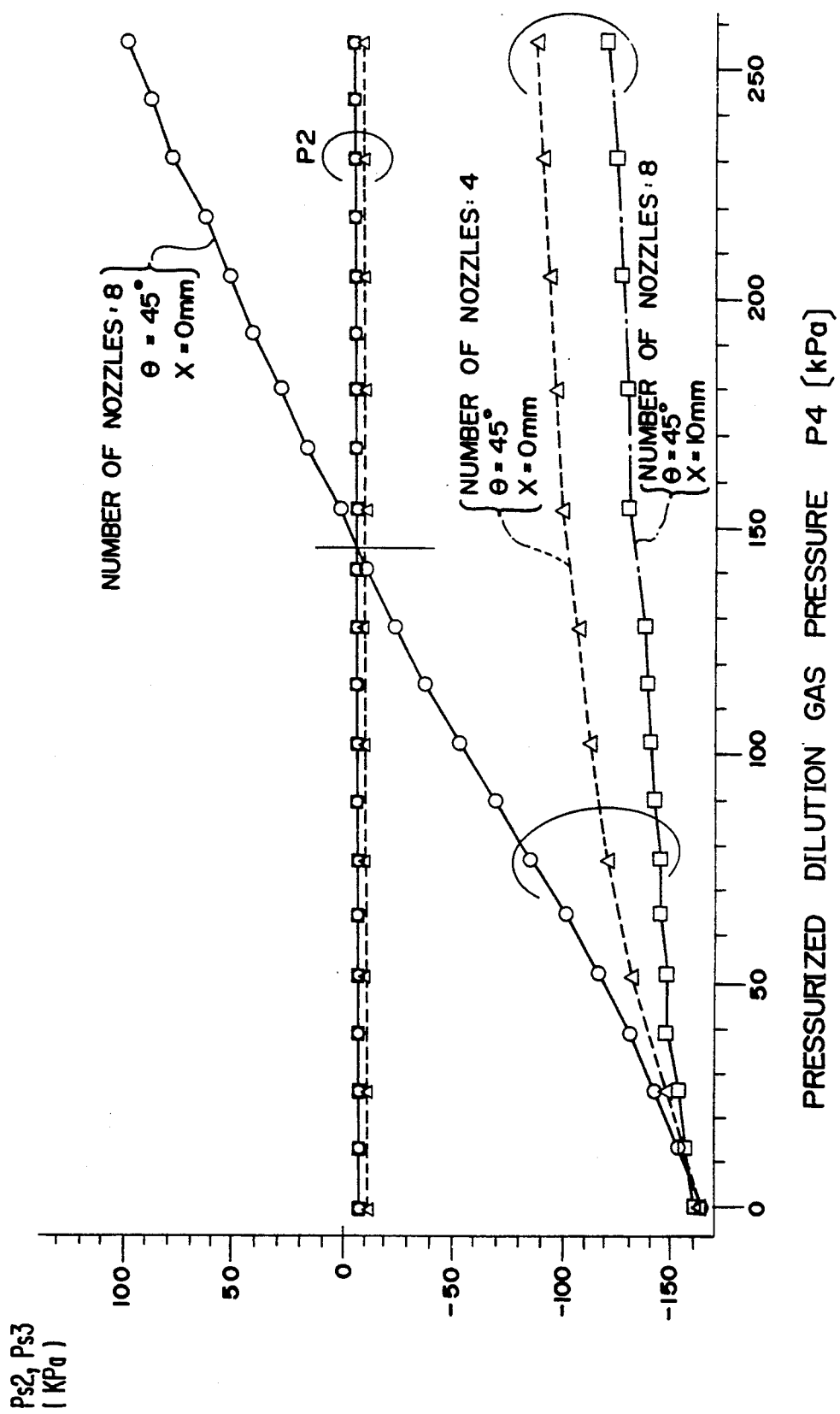

When other structural details of the division ratio control nozzles 10 in the system shown in FIG. 1 are changed, data shown in FIGS. 8 and 9 are obtained.

More specifically, a curve plotted with a series of squares in FIG. 8 is obtained when there are eight division ratio control nozzles, the angle $\theta$ is $\theta=60°$, and the distance X is X=0 mm. A curve plotted with a series of circles in FIG. 8 is obtained when there are eight division ratio control nozzles, the angle $\theta$ is $\theta=45°$, and the distance X is X=0 mm. A curve plotted with a series of triangles in FIG. 8 is obtained when there are eight division ratio control nozzles, the angle $\theta$ is $\theta=30°$, and the distance X is X=0 mm.

With the curve plotted with squares, the static pressures Ps2, Ps3 are equalized when the pressurized dilution gas pressure P4 is P4=1.0 kg/cm$^2$, and reach peak values when the pressure P4 is P4=1.8 kg/cm$^2$, and thereafter are lowered. According to the curve plotted with circles, the static pressures Ps2, Ps3 are equalized when P4=1.5 kg/cm$^2$ and remain linear up to P4=2.5 kg/cm$^2$. With the curve plotted with triangles, the static pressures Ps2, Ps3 are not equalized even when P4=2.5 kg/cm$^2$. Therefore, the division ratio control nozzles represented by the curve plotted with circles are most preferable, and the division ratio control nozzles represented by the curve with squares are second most preferable.

FIG. 9 shows other curves including the same curve plotted with circles as shown in FIG. 8. In FIG. 9, a curve plotted with triangles is obtained when there are four division ratio control nozzles, the angle $\theta$ is $\theta=45°$, and the distance X is X=0 mm, and a curve plotted with squares is obtained when there are eight division ratio control nozzles, the angle $\theta$ is $\theta=45°$, and the distance X is X=10 mm. According to these curves, the static pressures Ps2, Ps3 are not equalized even when P4=2.5 km/cm$^2$.

It can be seen from FIGS. 8 and 9 that the number of division ratio control nozzles should be eight rather than four, the angle $\theta$ ranging from 40° to 50° is practical, and the distance X=0 mm is practical. With the division ratio control nozzles 10 employed, when the pressurized dilution gas pressure P4 is varied, the static pressure Ps2 at the outlet of the inlet pipe 4 is varied. Therefore, when the pressurized dilution gas pressure P4 is controlled so that the static pressures Ps2, Ps3 are equalized to each other, an exhaust gas can be introduced into the dilution tunnel 5 at a rate which is always constant with respect to the rate of the total exhaust gas introduced into the system, irrespective of fluctuations in the rate of the total exhaust gas.

In the multiple flow-dividing dilution tunnel system shown in FIG. 1, pressure information of the static pressure Ps2 at the outlet of the inlet pipe 4, the static pressure Ps3 at the outlet of the flow divider 2, and the pressurized dilution gas pressure P4, as detected by the static pressure detectors 20, 21, 23, is supplied to the controller 12, and the controller 12 controls the discharge rate control valve 18 such that the static pressures Ps2, Ps3 will be equalized to each other.

Figure 11:
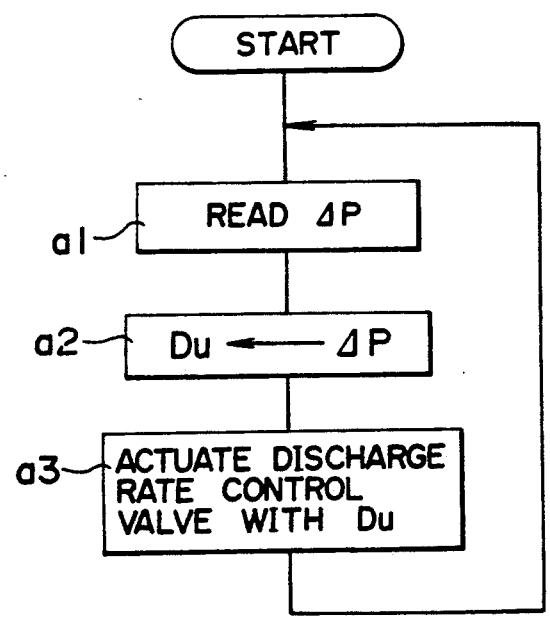
FIG. 11 is a flowchart of a pressure control sequence effected by the multipipe flow-dividing dilution tunnel system shown in FIG. 1.

FIG. 11 shows a pressure control sequence which is carried out by the controller 12 in the multipipe flow-dividing dilution tunnel system shown in FIG. 1.

The butterfly valve 24 is actuated in advance by the actuator 26 so that the static pressures Ps2, Ps3 are related to each other as: Ps2≦Ps3. The pressure difference $\Delta P$ between the static pressures Ps2, Ps3 is detected by the differential pressure detector 11 at all times in a step a1.

Figure 10:
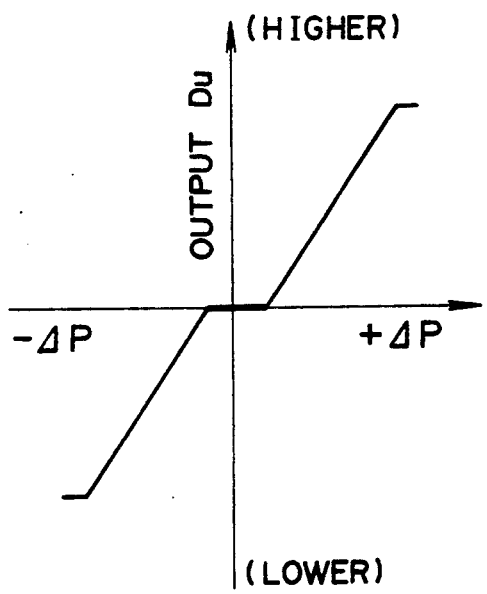
FIG. 10 is a diagram showing a map for calculating an output of a discharge rate control valve with a controller in the multipipe flow-dividing dilution tunnel system shown in FIG. 1.

The controller 12 reads the detected differential pressure $\Delta P$, and determines, from the map shown in FIG. 10, an output value Du to produce a pressurized dilution gas pressure P4 which is high enough to eliminate the differential pressure $\Delta P$ in a step a2. Then, the controller 12 applies the output value Du in the form of an electric signal to the discharge rate control valve 18 in a step a3 to change the actual value of the pressurized dilution gas pressure P4, thereby regulating the static pressure Ps2 until the static pressures Ps2, Ps3 will automatically be equalized to each other.

When the static pressures Ps2, Ps3 are equalized to each other, since the inlet pipe 4 and the flow-dividing pipes 1 of the multipipe flow divider 2 are dimensionally and hydrodynamically in the completely same conditions, the exhaust gases flow at the same rate through the pipes 1, 4 irrespective of fluctuations of the rate of the entire exhaust gas which is introduced into the multipipe flow-dividing dilution tunnel system. The exhaust gas is divided at a constant division ratio at all times, and the divided exhaust gas is introduced into the dilution tunnel 5 in which the exhaust gas is diluted. The diluted exhaust gas is thereafter sampled and analyzed for its constituents.

In the multipipe flow-dividing dilution tunnel system shown in FIG. 1, the exhaust gas from the multipipe flow divider 2 is discharged into atmosphere through a flue (not shown). To such a flue, there are connected a plurality of test benches. Therefore, exhaust gases from a plurality of automobile engines on the test benches are discharged into the flue. When such a plurality of automobile engines are tested simultaneously, the exhaust gases may intefere with each other through the flue, and may not be accurately divided for sampling and analysis.

Figure 12:
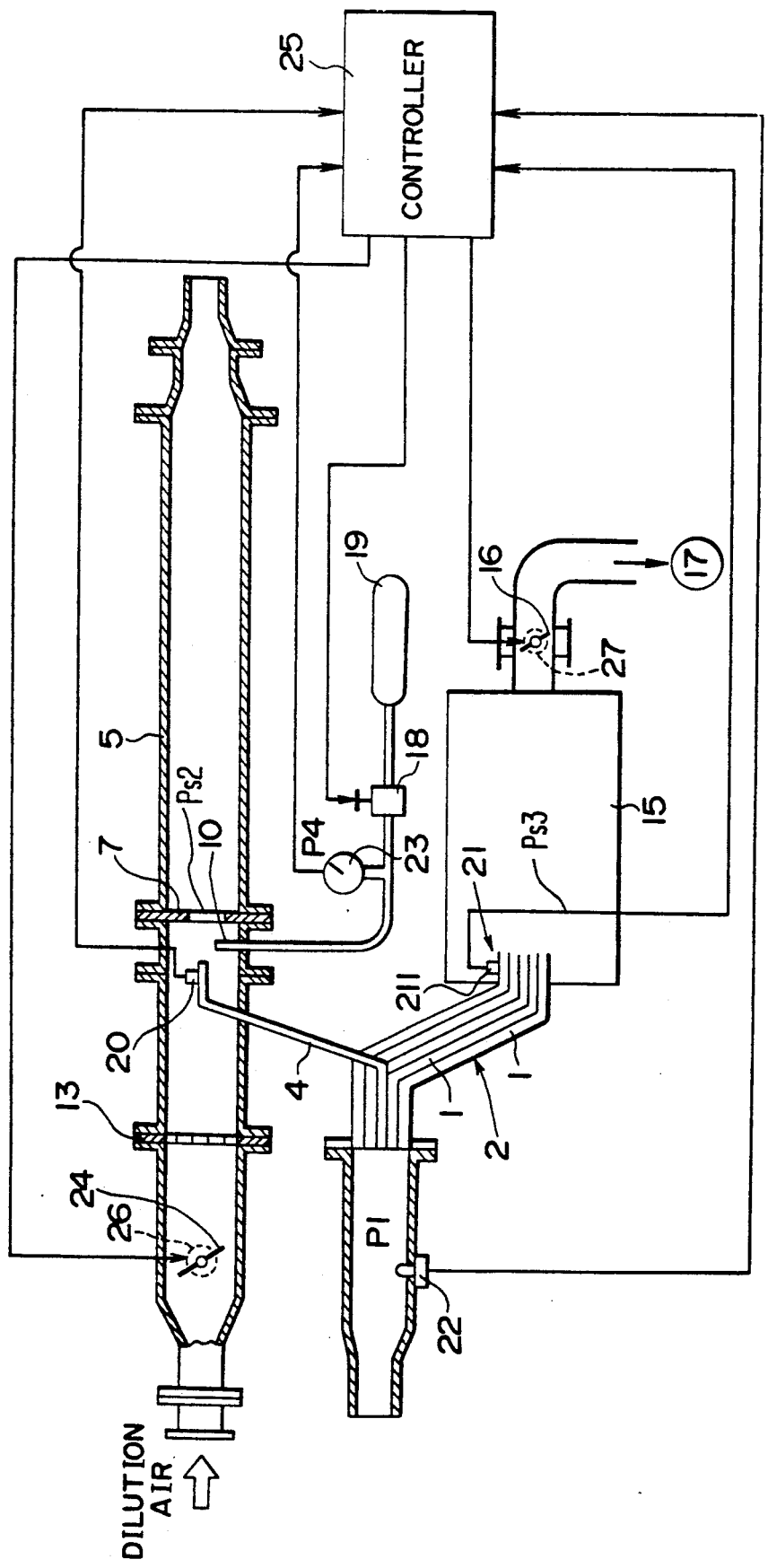
FIG. 12 is a schematic cross-sectional view, partly in block form, of a multipipe flow-dividing dilution tunnel system according to another embodiment of the present invention.

FIG. 12 shows a multipipe flow-dividing dilution tunnel system according to another embodiment of the present invention. In the multipipe flow-dividing dilution tunnel system shown in FIG. 12, the exhaust gas from the multipipe flow divider 2 is introduced into a flue 17 through a surge tank 15 and a butterfly valve 16, and then discharged into atmosphere from the flue 17. Those parts in FIG. 12 which are identical to those parts shown in FIG. 1 will be denoted by identical reference numerals, and will not be described in detail.

In FIG. 12, the multipipe flow-dividing dilution tunnel system has static pressure detectors 20, 21, 22, 23 for detecting a static pressure Ps2 at the outlet of the inlet pipe 2, a static pressure Ps3 at the outlet of the multipipe flow divider 2, a static pressure detector 22 for detecting a pressure P1 at the inlet of the multipipe flow divider 2, and a static pressure detector 23 for detecting the pressure P4 of the pressurized dilution gas. Detected signals from the static pressure detectors 20, 21, 22, 23 are applied to a controller 25. The pressurized dilution gas pressure P4 is controlled by the controller 25 through a discharge rate control valve 18.

A butterfly valve 24 disposed in an upstream portion of a dilution tunnel 5 and a butterfly valve 16 located downstream of the surge tank 15 are connected to conventional electric actuators 26, 27, respectively, which are controlled by the controller 25 to vary the opening of the valves 24, 16.

Figure 3:
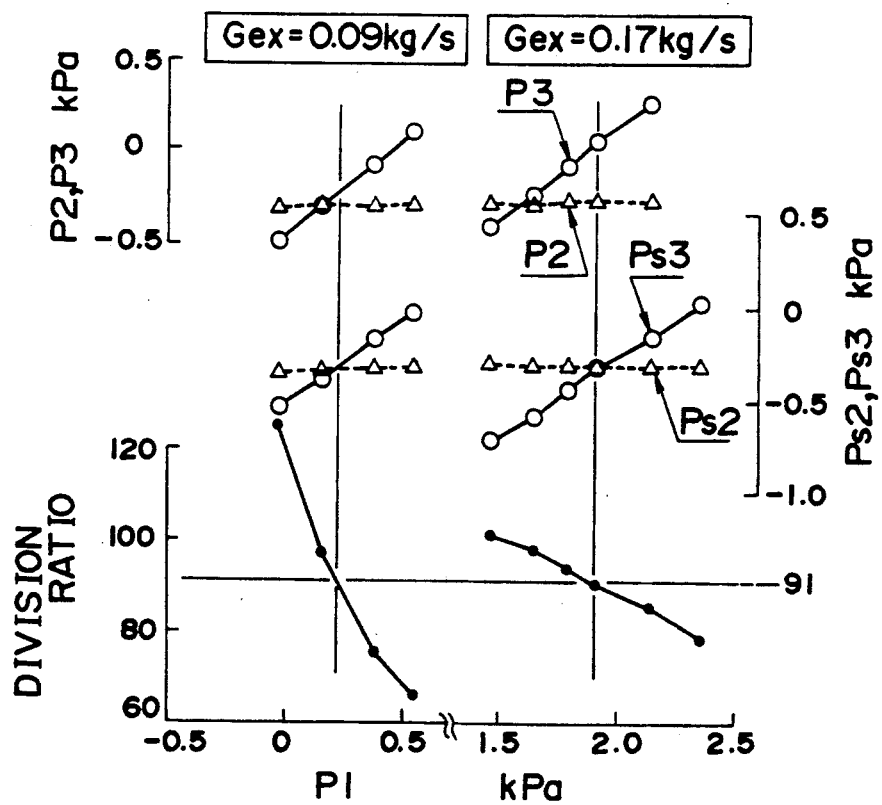
FIG. 3 is a diagram showing the manner in which the pressures detected by static pressure detectors change.
Figure 4A:
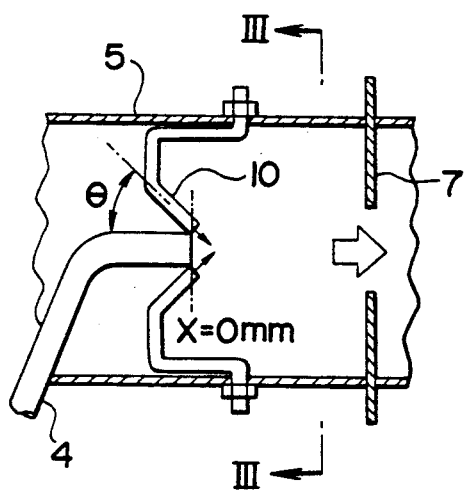
FIGS. 4A and 4B are fragmentary cross-sectional views showing an encircled portion II in FIG. 1.
Figure 4B:
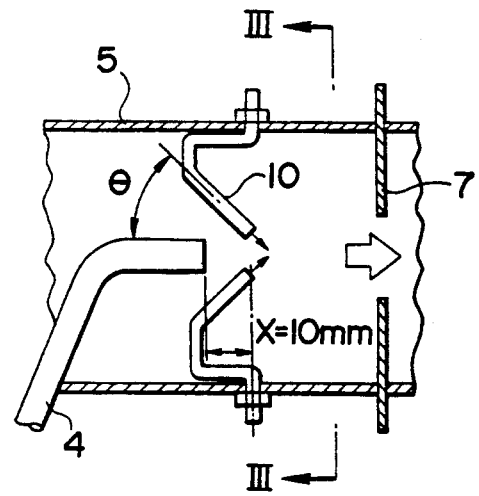
Figure 5A:
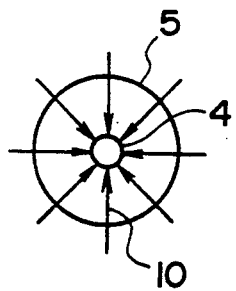
FIGS. 5A and 5B are cross-sectional views taken along line III—III of FIGS. 4A and 4B, respectively.
Figure 5B:
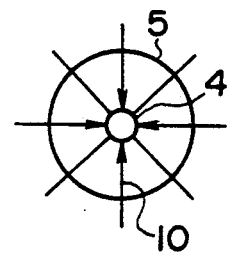

FIG. 3 shows the manner in which the pressures in the multipipe flow-dividing dilution tunnel system shown in FIG. 12 vary, the multipipe flow divider 2 having 91 flow-dividing pipes and hence the division ratio for the exhaust gas being 91. In obtaining the data shown in FIG. 3, the pressure P3 in the surge tank 15 was varied by adjusting the opening of the butterfly valve 16 at the outlet of the surge tank 15. As a result, the static pressure P1, the static pressure Ps2, the static pressure Ps3, and the pressure P2 in front of the mixing orifice 7 varied as shown in FIG. 3.

When the static pressures Ps2, Ps3 are equal to each other, the division ratio was exactly 91, and the pressure P2 is not equal to the pressure P3. The higher the pressure P1, the greater the deviation between the pressures P2, P3. It was confirmed that reliable test results were obtained when the multipipe flow-dividing dilution tunnel system was controlled based on the static pressures Ps2, Ps3.

Figure 13:
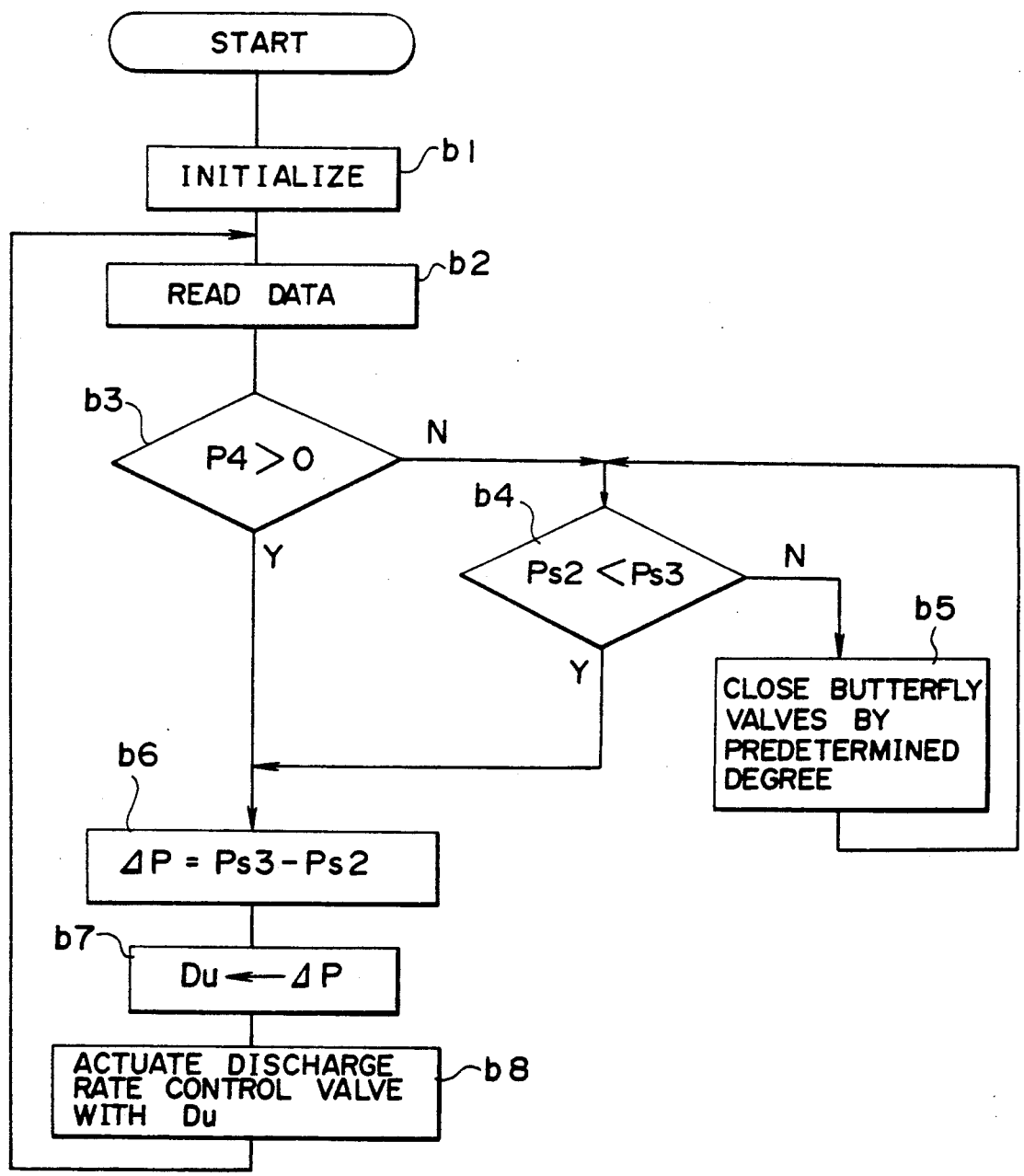
FIG. 13 is a flowchart of a pressure control sequence effected by the multipipe flow-dividing dilution tunnel system shown in FIG. 12.
Figure 14:
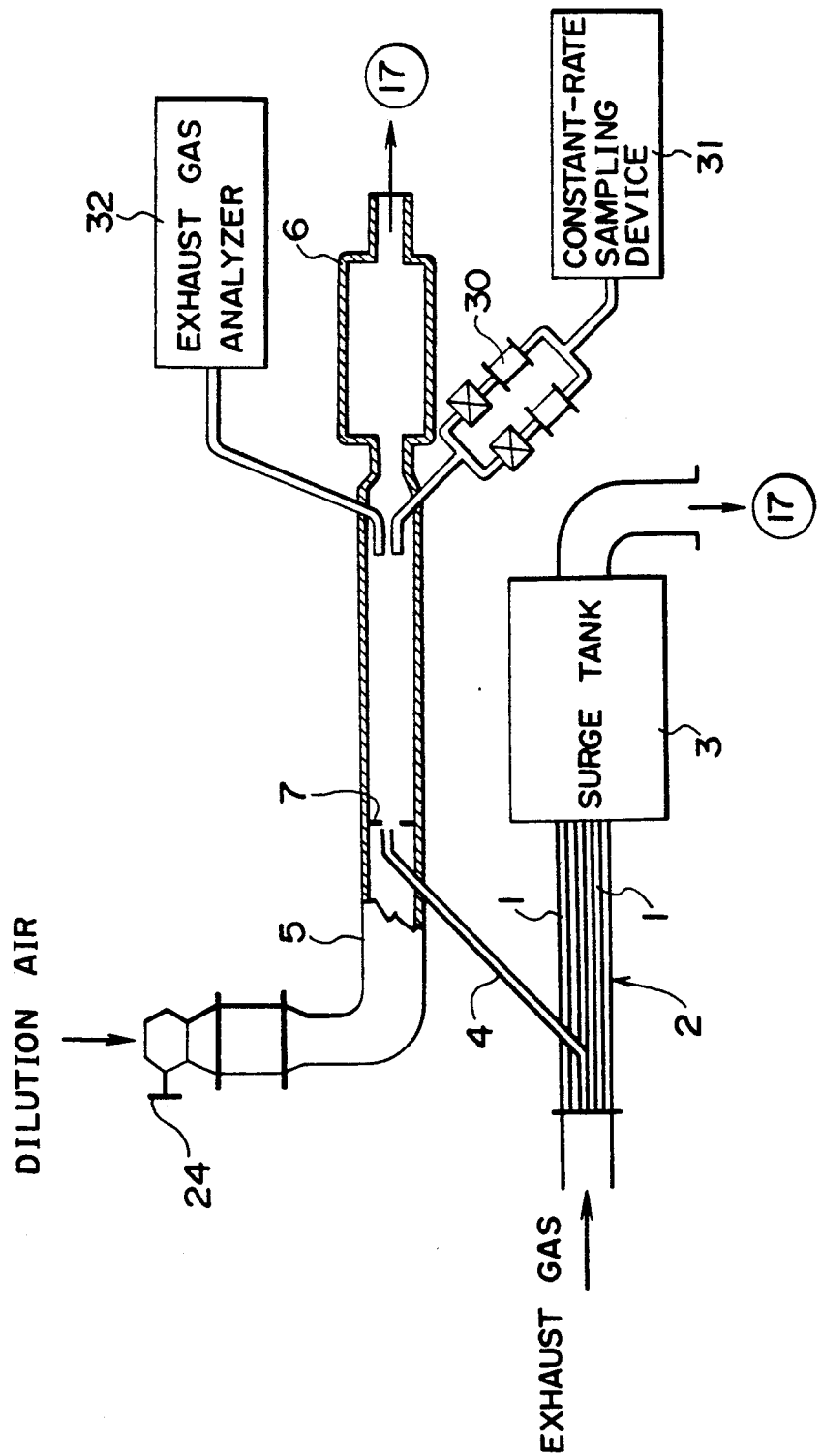
FIG. 14 is a schematic view of a conventional flow-dividing dilution tunnel system.

The controller 25 carries out a pressure control sequence as shown in FIG. 13.

When the pressure control sequence is started, the controller 25 initializes various components, such as closing the discharge rate control valve 18 and operating the actuators 26, 27 into fully open positions in a step b1. Then, the controller 25 reads various data from the static pressure detectors, etc. in a step b2. In a step b3, the controller 25 determines whether the pressurized dilution gas pressure P4 is supplied or not. If not, control goes to a step b4 which determines whether the static pressure Ps3 is higher than the static pressure Ps2 or not. If the static pressure Ps3 is higher than the static pressure Ps2, then control goes to a step b6, and if not, control goes to a step b5 in which the butterfly valve 24 is closed by a predetermined degree, after which the step b4 is executed again.

If the pressurized dilution gas pressure P4 is supplied in the step b3, then the controller 25 calculates $\Delta P = Ps3 - Ps2$ in the step b6. If $\Delta P > 0$, then controller 25 determines an output value Du to increase the pressure P4 in a step b7, and actuates the discharge rate control valve 18 with the output value Du in a step b8. If $\Delta P<0$, then the controller 25 determines an output value Du to reduce the pressure P4 in the step b7, and actuates the discharge rate control valve 18 with the output value Du in the step b8. If $\Delta P=0$, then control goes to end.

With the above pressure control sequence, the differential pressure $\Delta P$ is eliminated, thereby automatically equalizing the static pressures Ps2, Ps3.

Consequently, the introduced exhaust gas is divided at a constant division ratio at all times, and the divided exhaust gas is introduced into the dilution tunnel 5 in which the exhaust gas is diluted. The diluted exhaust gas is thereafter sampled and analyzed for its constituents.

Although certain preferred embodiments have been shown and described, it should be understood that many changes and modifications may be made therein without departing from the scope of the appended claims.

What is claimed is:

1. A multipipe flow-dividing dilution tunnel system comprising:
   a multipipe flow divider composed of a plurality of flow-dividing pipes having the same diameter and length as each other, for supplying a gas to be inspected therethrough;
   a dilution tunnel for introducing a dilution gas from an upstream end thereof, one of said flow-dividing pipes extending out of said multipipe flow divider and having a downstream end portion extending as an inlet pipe into said dilution tunnel, whereby a gas divided by and introduced through said inlet pipe into said dilution tunnel is diluted by the dilution gas introduced into said dilution tunnel, so that the diluted gas can be sampled and analyzed for constituents thereof; and
   a plurality of division ratio control nozzles disposed in said dilution tunnel immediately downstream of an outlet of said inlet pipe and arranged symmetrically around a central axis of said outlet of the inlet pipe, said division ratio control nozzles having respective nozzle holes for ejecting a pressurized dilution gas toward a position downstream of the outlet of said inlet pipe.

2. A multipipe flow-dividing dilution tunnel system according to claim 1, further including a surge tank connected to said flow-dividing pipes except for said inlet pipe, for combining gases flowing out of said flow-dividing pipes, said surge tank being connected to a passage vented to atmosphere through a valve.

3. A multipipe flow-dividing dilution tunnel system according to claim 1, wherein each of said division ratio control nozzles has a central axis which is angularly spaced from the central axis of the outlet of said inlet pipe by an angle ranging from 40° to 50°.

4. A multipipe flow-dividing dilution tunnel system comprising:
   a multipipe flow divider composed of a plurality of flow-dividing pipes having the same diameter and length as each other, for supplying a gas to be inspected therethrough;
   a dilution tunnel for introducing a dilution gas from an upstream end thereof, one of said flow-dividing pipes extending out of said multipipe flow divider and having a downstream end portion extending as an inlet pipe into said dilution tunnel, whereby a gas divided by and introduced through said inlet pipe into said dilution tunnel is diluted by the dilution gas introduced into said dilution tunnel, so that the diluted gas can be sampled and analyzed for constituents thereof;
   a plurality of division ratio control nozzles disposed in said dilution tunnel immediately downstream of an outlet of said inlet pipe and arranged symmetrically around a central axis of said outlet of the inlet pipe, said division ratio control nozzles having respective nozzle holes for ejecting a pressurized dilution gas toward a position downstream of the outlet of said inlet pipe;
   a discharge rate control valve for regulating a rate at which the pressurized dilution gas is ejected from said division ratio control valves;
   a source of the pressurized dilution gas, said source being connected to said division ratio control nozzles through said discharge rate control valve; and
   control means connected to said discharge rate control valve, for controlling said discharge rate control valve so that a static pressure at the outlet of said inlet pipe and a static pressure at the outlet of said multipipe flow divider will be equalized to each other.

5. A multipipe flow-dividing dilution tunnel system according to claim 1 or 4, further including a plurality of static pressure detectors disposed respectively at the outlet of said inlet pipe and the outlet of said multipipe flow divider, said static pressure detectors being positioned upstream from outlet ends of said inlet pipe and said multipipe flow divider by a distance which is equal to at least the inside diameter of said flow-dividing pipes including the inlet pipe.

6. A multipipe flow-dividing dilution tunnel system according to claim 1 or 4, further including a plurality of static pressure detectors disposed respectively at the outlet of said inlet pipe and the outlet of said multipipe flow divider, each of said static pressure detectors having a plurality of detector units equally spaced axially from outlet ends of said inlet pipe and said multipipe flow divider, for transmitting average static pressure information to said control means.

* * * * *